US010215723B2

United States Patent
Yang et al.

(10) Patent No.: US 10,215,723 B2
(45) Date of Patent: Feb. 26, 2019

(54) SYSTEM FOR DETERMINING THE ADIABATIC STRESS DERIVATIVE OF TEMPERATURE FOR ROCK

(71) Applicant: SOUTH CHINA SEA INSTITUTE OF OCEANOLOGY, CHINESE ACADEMY OF SCIENCES, Guangzhou, Guangdong (CN)

(72) Inventors: Xiaoqiu Yang, Guangzhou (CN); Weiren Lin, Nankoku (JP); Osamu Tadai, Nankoku (JP); Xin Zeng, Guangzhou (CN); Xiaobin Shi, Guangzhou (CN); Ziying Xu, Guangzhou (CN)

(73) Assignee: SOUTH CHINA SEA INSTITUTE OF OCEANOLOGY, CHINESE ACADEMY OF SCIENCES, Guangzhou, Guangdong (CN)

( * ) Notice: Subject to any disclaimer, the term of this patent is extended or adjusted under 35 U.S.C. 154(b) by 148 days.

(21) Appl. No.: 15/511,699

(22) PCT Filed: Mar. 9, 2016

(86) PCT No.: PCT/CN2016/076016
§ 371 (c)(1),
(2) Date: Mar. 16, 2017

(87) PCT Pub. No.: WO2017/140006
PCT Pub. Date: Aug. 24, 2017

(65) Prior Publication Data
US 2018/0038812 A1 Feb. 8, 2018

(30) Foreign Application Priority Data
Feb. 17, 2016 (CN) .......................... 2016 1 0089849

(51) Int. Cl.
G01N 25/48 (2006.01)
G01N 3/60 (2006.01)
(Continued)

(52) U.S. Cl.
CPC .......... *G01N 25/4846* (2013.01); *G01N 3/08* (2013.01); *G01N 3/60* (2013.01); *G01N 25/16* (2013.01);
(Continued)

(58) Field of Classification Search
CPC ........ G01N 25/4846; G01N 3/60; G01N 3/08; G01N 33/24; G01N 25/16;
(Continued)

(56) References Cited

U.S. PATENT DOCUMENTS 4,606,227 A * 8/1986 Walters ................... E21B 49/00
73/865.6
6,247,358 B1 * 6/2001 dos Santos ............. E21B 25/08
166/282
(Continued)

FOREIGN PATENT DOCUMENTS

CN 101482009 A 7/2009
CN 101949803 A 1/2011
(Continued)

OTHER PUBLICATIONS

English machine translation for document JP 08247978.*
(Continued)

*Primary Examiner* — Daniel S Larkin
*Assistant Examiner* — Anthony W Megna Fuentes
(74) *Attorney, Agent, or Firm* — Westerman, Hattori, Daniels & Adrian, LLP

(57) ABSTRACT

A system for determining an adiabatic stress derivative of temperature for rock includes two pressure vessels containing a rock sample unit. The two pressure vessels are both
(Continued)

filled with silicon oil. Bottoms of the pressure vessels are communicated with each other through an oil pipe. Each of the pressure vessels is communicated with a booster pump through an oil inlet pipe, and is provided with a pressure relief pipe at its top. Each of the oil pipe, the oil inlet pipes, and the pressure relief pipes is respectively provided with a drain valve. Each of the oil inlet pipes is respectively provided with a pressure sensor. Each of the rock sample units is respectively encapsulated in a rubber sleeve immersed in the silicone oil, and each rock sample is provided with temperature sensors on a surface and in a center thereof.

1 Claim, 2 Drawing Sheets

(51) Int. Cl.
*G01N 3/08* (2006.01)
*G01N 33/24* (2006.01)
*G01N 25/16* (2006.01)

(52) U.S. Cl.
CPC ..... *G01N 33/24* (2013.01); *G01N 2203/0075* (2013.01); *G01N 2203/0232* (2013.01)

(58) Field of Classification Search
CPC ... G01N 2203/0232; G01N 2203/0075; G01N 25/20; G01N 25/48

USPC .................. 73/38, 794, 798, 818–819, 865.6
See application file for complete search history.

(56) References Cited

U.S. PATENT DOCUMENTS

| | | | |
|---|---|---|---|
| 6,401,523 | B1 | 6/2002 | Fernandes et al. |
| 6,799,471 | B1 * | 10/2004 | Regimand ................ G01N 3/36 |
| | | | 137/386 |

FOREIGN PATENT DOCUMENTS

| | | |
|---|---|---|
| CN | 102539278 A | 7/2012 |
| CN | 103048261 A | 4/2013 |
| CN | 103487326 A | 1/2014 |
| CN | 104297287 A | 1/2015 |
| CN | 104749210 A | 7/2015 |
| CN | 105158115 A | 12/2015 |
| JP | 08247978 A * | 9/1996 |

OTHER PUBLICATIONS

Deng et al., "The Study on the Variation of Thermal State of Rocks Caused by the Variation of Stress State of Rocks," Earthquake Research in China, vol. 13, No. 2, Jun. 1997, pp. 179-185 (7 pages, including English abstract).

* cited by examiner

SYSTEM FOR DETERMINING THE ADIABATIC STRESS DERIVATIVE OF TEMPERATURE FOR ROCK

TECHNICAL FIELD

The present invention relates to the field of physical property determination of rocks, and particularly to a system for determining the adiabatic stress derivative of temperature for rock.

BACKGROUND OF THE INVENTION

Usually, stress change occurs during tectonic activities (such as mantle convection, plate tectonics, volcanic eruption and earthquake), and will induce temperature change across the earth's interior, which is described by the following equation:

$$\Delta T = \frac{-\alpha}{\rho c_p} \cdot T_0 \cdot \Delta \sigma \qquad (1)$$

where $T_0$ denotes the absolute temperature, $(\rho c_p)$ denotes the volumetric heat capacity, a is the coefficient of linear expansion, and $\Delta\sigma$ denotes the change in principal stress. Since the magnitude of the temperature change in response to the stress change varies in different kinds of rocks, to determine the adiabatic stress derivative of temperature $(\Delta T/\Delta\sigma)$ for different rocks will help to understand the mechanism of temperature change of the earth's interior, and provide theoretical basis for stress and temperature monitoring and earthquake prevention in active tectonic zones.

At present, when determining the temperature response to the stress change of rocks, temperature sensors are usually attached to the surface of the rock samples and in contact with the air, such that the system is open to the external environment, and it is impossible to achieve instant loading and unloading due to the restriction of stress loading units. Thus, it is impossible to achieve stress loading and unloading under adiabatic condition and thereby the results of such determination will be affected significantly by the heat exchange between the rock sample and the air.

SUMMARY OF THE INVENTION

The objective of the present invention is to provide a system for determining the adiabatic stress derivative of temperature for rock, which allows loading and unloading under adiabatic condition and achieves real-time monitoring of confining pressure of pressure vessels and temperature change of the rocks to obtain the adiabatic stress derivative of temperature for rock $(\Delta T/\Delta\sigma)$.

The system of the present invention comprises two pressure vessels both filled with silicon oil, and disposed in each pressure vessel is a rock sample unit. Bottoms of the pressure vessels are communicated with each other through an oil pipe. Each of the pressure vessels is communicated with a booster pump through an oil inlet pipe, and provided with a pressure relief pipe at its top. Each of the oil pipe, the oil inlet pipes and the pressure relief pipes is respectively provided with a drain valve. Each of the oil inlet pipes is respectively provided with a pressure sensor, which is configured to monitor the confining pressure in the pressure vessel. Each of the rock sample units is respectively encapsulated in a rubber sleeve immersed in the silicone oil, and each rock sample is provided with temperature sensors on a surface and in a center thereof.

Further disposed in the silicone oil in each of the pressure vessels is a temperature sensor.

The system further comprises:

a confining pressure collecting module, communicated with the pressure sensors, and configured to collect confining pressure data inside the pressure vessels;

a temperature collecting module, communicated with the temperature sensors, and configured to collect temperature change data of the rock samples and the silicone oil in the pressure vessels;

a processing module, communicated with the booster pumps, the confining pressure collecting module and the temperature collecting module respectively, and configured to control the confining pressure inside the pressure vessels, and calculate the adiabatic stress derivative of temperature for rock based on the confining pressure data and the temperature change data.

The above system has a simple and feasible design. As the rock samples are provided with temperature sensors on the surface and in the center thereof, encapsulated in the rubber sleeves and immersed in the silicone oil in the pressure vessels, we can obtain $(\Delta T/\Delta\sigma)$ by the following process: first raising the confining pressure in one of the pressure vessels to a given value (e.g., 130 MPa) with the booster pump; when the whole system reaches a temperature equilibrium, rapidly opening the drain valve between the two pressure vessels, such that within 1-2 seconds the confining pressure in one vessel decreases instantly while the confining pressure in the other vessel rises instantly; within 10-20 seconds after the rapidly opening the drain valve, the temperature of the centers of the rock samples are not yet affected by the temperature change of the silicone oil, such that the adiabatic loading and unloading of the rock samples are achieved and thereby we can obtain $(\Delta T/\Delta\sigma)$ by real-time collecting and analyzing the change in confining pressure in the pressure vessels and temperature in the centers of the rock samples. Furthermore, the system can perform such determination on two rock samples simultaneously.

Figure 1:
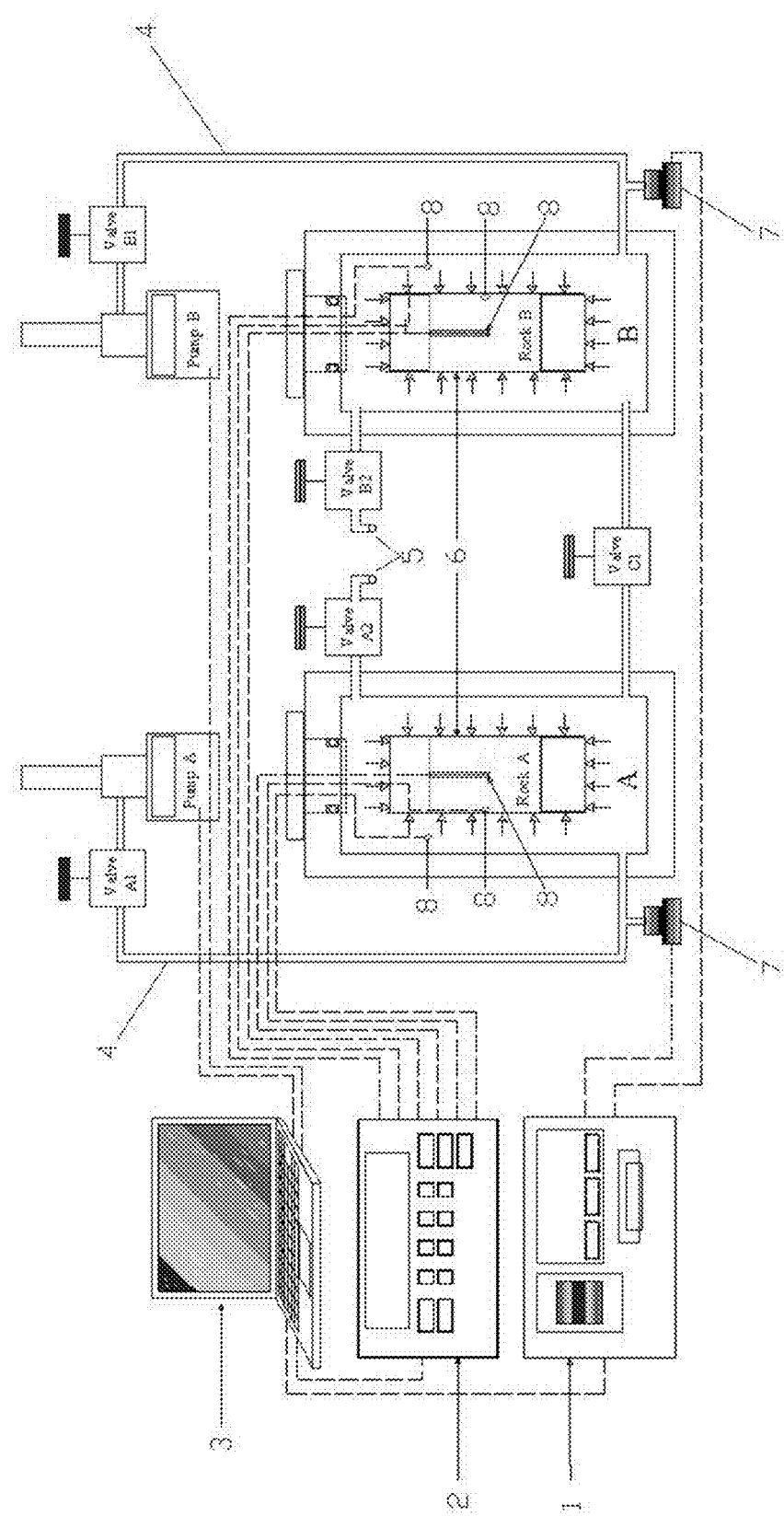
FIG. 1 is a schematic diagram of the system of the present invention.

Reference characters in the drawings: 1: confining pressure collecting module; 2: temperature collecting module; 3: processing module; 4: oil inlet pipe; 5: pressure relief pipe; 6: rubber sleeve; 7: pressure sensor; 8: temperature sensor.

DETAILED DESCRIPTION OF THE EMBODIMENT

Further characteristics and advantages of the present invention will be more readily apparent from the below detailed description of the drawings and the embodiment.

Embodiment

As shown in FIG. 1, the system of the present invention comprises two pressure vessels both filled with silicon oil, and disposed in each pressure vessel is a rock sample unit. Bottoms of the pressure vessels are communicated with each other through an oil pipe. Each of the pressure vessels is respectively communicated with a booster pump through an oil inlet pipe 4, and provided with a pressure relief pipe 5 at its top. Each of the oil pipe, the oil inlet pipes 4 and the pressure relief pipes 5 is respectively provided with a drain valve, and each of the oil inlet pipes 4 is respectively provided with a pressure sensor 7 to monitor the confining pressure in each pressure vessel. Each of the rock sample units is respectively encapsulated in a rubber sleeve 6 immersed in the silicone oil, and provided on a surface and in a center of each rock sample respectively is a temperature sensor 8.

Further disposed in the silicone oil in each of the pressure vessels is a temperature sensor 8.

The system further comprises:

a confining pressure collecting module 1, communicated with the pressure sensors 7, and configured to collect confining pressure data inside the pressure vessels;

a temperature collecting module 2, communicated with the temperature sensors 8, and configured to collect temperature change data of the rock samples and the silicone oil in the pressure vessels;

a processing module 3, communicated with the booster pumps, the confining pressure collecting module 1 and the temperature collecting module 2 respectively, and configured to control the confining pressure inside the pressure vessels, and calculate the ratio between the adiabatic stress derivative of temperature for rock based on the confining pressure data and the temperature change data.

Specifically, the system in this embodiment mainly comprises:

1) two booster pumps, Pump A and Pump B;
2) two pressure vessels A and B, both filled with silicone oil;
3) five drain valves, A1, A2, B1, B2 and C1, respectively provided at the oil inlet pipes 4, pressure relief pipes 5 and the oil pipe (stainless steel pipes);
4) two cylindrical rock samples, Rock A and Rock B; each sample is provided temperature sensors 8 with high stability and high resolution on the surface and in the center thereof respectively, and after being liquid-tight encapsulated in a rubber sleeve 6, put in the silicone oil; in each vessel, a temperature sensors 8 with high stability and high resolution is disposed in the silicone oil;
5) two pressure sensors 7, which is configured to detect the change in confining pressure in the two vessels;
6) a temperature collecting module 2;
7) a confining pressure collecting module 1;
8) a processing module 3, which can be a computer.

In practice, we can obtain ($\Delta T/\Delta\sigma$) by the following process: first raising the confining pressure in one of the pressure vessels to a given value (e.g., 130 MPa) with the booster pump thereof; when the whole system reaches a temperature equilibrium, rapidly opening the drain valve between the two pressure vessels, such that within 1-2 seconds the confining pressure in one vessel decreases instantly while the confining pressure in the other vessel rises instantly; within 10-20 seconds after the rapidly opening the drain valve, the temperature in the centers of the rock samples are not yet affected by the temperature change of the silicone oil, such that the adiabatic loading and unloading of the rock samples are achieved and thereby we can obtain the derivative ($\Delta T/\Delta\sigma$) by real-time collecting the confining pressure data and the temperature change data.

Specifically, the present invention can be achieved by the following steps:

Step 1: Disposing temperature sensors 8 on the surface and in the center of each prepared cylindrical rock sample, which is then encapsulated in a liquid-tight encapsulation with a rubber sleeve 6.

Step 2: Disposing the encapsulated rock samples into the two pressure vessels respectively, and then sealing the vessels. As shown in FIG. 1, the vessels and the booster pumps are connected through stainless steel pipes, the temperature sensors 8 are communicated with the temperature collecting module 2, and the pressure sensors 7 are communicated with the confining pressure collecting module 1. Then turning on the two modules to start collecting data.

Step 3: Opening the drain valve A1 while the other four drain valves (A2, B1, B2 and C1) remain closed, and switching on the booster pump A to raise the confining pressure in the pressure vessel A to a given value (e.g., 130 MPa).

Step 4: After 3-6 hours, when the whole system reaches a temperature equilibrium, closing the drain valve A1 and rapidly opening the drain valve C1 while the valves A2, B1 and B2 remain closed, such that the confining pressure in the vessel A decreases instantly while the confining pressure in the vessel B rises instantly.

Step 5: After 3-6 hours, when the whole system reaches a temperature equilibrium again, opening the drain valve B1 while the other four drain valves (A1, A2, B2 and C1) are closed, and switching on the booster pump B to raise the confining pressure in the pressure vessel B to a given value (e.g., 130 MPa).

Step 6: After 3-6 hours, when the whole system reaches a temperature equilibrium again, closing the drain valve B1 and rapidly opening the drain valve C1 while the valves A1, A2 and B2 remain closed, such that the confining pressure in the vessel B decreases instantly while the confining pressure in the vessel A rises instantly.

During the above process, rapid loading and unloading have been performed on both of the rock samples Rock A and Rock B, and the temperature data and the confining data have been real-time monitored and recorded. Within 10-20 seconds after the rapidly opening the drain valve, since the temperature in the centers of the rock samples are not yet affected by the temperature change of the silicone oil, the center of rock sample can be identified by adiabatic condition. We can obtain ($\Delta T/\Delta\sigma$) by real-time collecting and analyzing the change in confining pressure and temperature.

Figure 2:
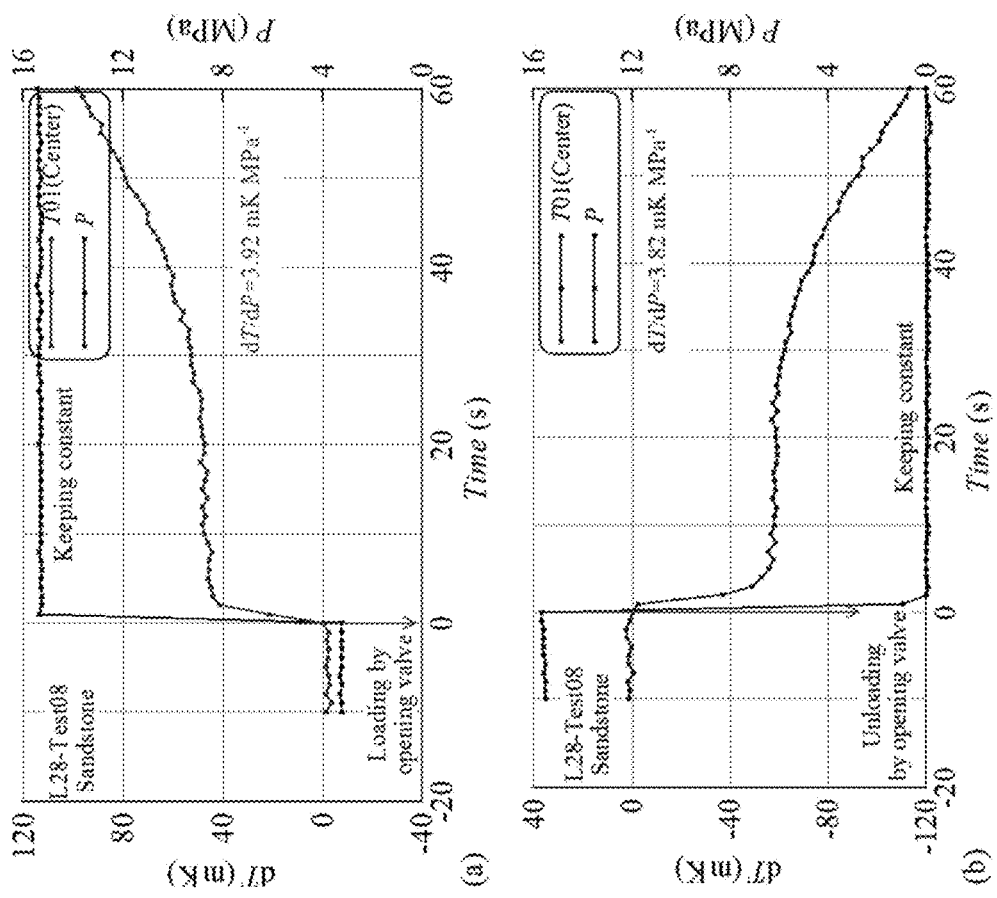
FIG. 2 shows the temperature response curves of a sandstone sample during rapid loading and unloading processes.

FIG. 2 shows the temperature response curves of a rapid loading process (FIG. 2a) and a rapid unloading process (FIG. 2b) on the sandstone sample (L28), which is collected from the Longmenshan Fault Zone. After the rapid loading (or unloading), an instant rise (or decrease) in temperature in the center of the sample is observed. Then the temperature doesn't change much until about 20 seconds later it rises (or decreases) gradually as affected by the temperature of the silicone oil. Results of the rapid loading process and the rapid unloading process are 3.92 mK/MPa and 3.82 mK/MPa respectively, with a relative error below 3%. We have performed the test on various kinds of rocks from different areas and all of the tests give good results, indicating that the system is feasible and stable, and makes it easier to perform a test on the temperature change of rocks in response to the adiabatic stress change.

In summary, the present invention allows the adiabatic loading and unloading of the rock samples, by which we can obtain ($\Delta T/\Delta\sigma$) by real-time collecting and analyzing the change in confining pressure and temperature of the rock samples. Furthermore, as two booster pumps and two vessels are provided, the system can perform adiabatic loading/unloading on two rock samples simultaneously, which significantly improves the efficiency.

The above detailed description is a specific explanation for feasible embodiments of the present invention. The embodiments are not used for limiting the scope of the present invention. Any equivalent or changes made on the basis of the present invention shall fall within the scope of the present invention.

The invention claimed is:

1. A system for determining an adiabatic stress derivative of temperature for rock, comprising:
   two pressure vessels both filled with silicon oil and having bottoms communicated with each other through an oil pipe, each of the pressure vessels communicating with a booster pump through an oil inlet pipe, each of the pressure vessels having a pressure relief pipe provided at a top of the pressure vessel, each of the oil pipe, the oil inlet pipes and the pressure relief pipes being respectively provided with a drain valve, and each of the oil inlet pipes being respectively provided with a pressure sensor;
   a rock sample disposed in each pressure vessel, the rock sample being encapsulated in a rubber sleeve immersed in the silicone oil, and the rock sample being provided with temperature sensors, at least one of the temperature sensors being located on a surface of the rock sample and at least one of the temperature sensors being located in a center of the rock sample;
   a temperature sensor disposed in the silicone oil in each of the pressure vessels;
   a confining pressure collecting module, communicated with the pressure sensors, and configured to collect confining pressure data inside the pressure vessels;
   a temperature collecting module, communicated with the temperature sensors, and configured to collect temperature change data of the rock sample and the silicone oil in the pressure vessels; and
   a processing module, communicated with the booster pumps, the confining pressure collecting module, and the temperature collecting module respectively, and configured to control the confining pressure inside the pressure vessels, and calculate the adiabatic stress derivative of temperature for rock based on the confining pressure data and the temperature change data.

* * * * *